(12) United States Patent
Vija et al.

(10) Patent No.: US 11,701,074 B2
(45) Date of Patent: Jul. 18, 2023

(54) COMPTON CAMERA WITH SEGMENTED DETECTION MODULES

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US); James Frank Caruba, Bartlett, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 64 days.

(21) Appl. No.: 17/250,575

(22) PCT Filed: Aug. 7, 2018

(86) PCT No.: PCT/US2018/045465
§ 371 (c)(1),
(2) Date: Feb. 4, 2021

(87) PCT Pub. No.: WO2020/032921
PCT Pub. Date: Feb. 13, 2020

(65) Prior Publication Data
US 2021/0290189 A1 Sep. 23, 2021

(51) Int. Cl.
*A61B 6/00* (2006.01)
*A61B 6/03* (2006.01)
(Continued)

(52) U.S. Cl.
CPC ............ *A61B 6/4417* (2013.01); *A61B 6/032* (2013.01); *A61B 6/037* (2013.01); *A61B 6/06* (2013.01);
(Continued)

(58) Field of Classification Search
CPC .......... A61B 6/032; A61B 6/037; A61B 6/06; A61B 6/4266; A61B 6/4275;
(Continued)

(56) References Cited

U.S. PATENT DOCUMENTS 2,999,951 A * 9/1961 Flynn ................... H02K 3/22
310/56
4,190,772 A * 2/1980 Dinwiddie ............ A61B 6/032
250/363.02
(Continued)

FOREIGN PATENT DOCUMENTS

EP 2060932 B1 3/2017
JP 2007101234 A 4/2007
(Continued)

OTHER PUBLICATIONS

Ordonez, Caesar E., Alexander Bolozdynya, and Wei Chang. "Doppler broadening of energy spectra in Compton cameras." Nuclear Science Symposium, 1997. IEEE. vol. 2. IEEE, 1997.
(Continued)

*Primary Examiner* — Blake C Riddick

(57) ABSTRACT

A Compton camera for medical imaging is divided into segments with each segment including part of the scatter detector, part of the catcher detector, and part of the electronics. The different segments may be positioned together to form the Compton camera arcing around part of the patient space. By using segments, any number of segments may be used to fit with a multi-modality imaging system.

20 Claims, 5 Drawing Sheets

(51) Int. Cl.
*A61B 6/06* (2006.01)
*G01T 1/29* (2006.01)

(52) U.S. Cl.
CPC .......... *A61B 6/4266* (2013.01); *A61B 6/4275* (2013.01); *A61B 6/4411* (2013.01); *A61B 6/4488* (2013.01); *A61B 6/483* (2013.01); *G01T 1/2985* (2013.01)

(58) Field of Classification Search
CPC ... A61B 6/4411; A61B 6/4417; A61B 6/4488; A61B 6/483; G01T 1/2985
See application file for complete search history.

(56) References Cited

U.S. PATENT DOCUMENTS

| | | | |
|---|---|---|---|
| 4,700,074 A | 10/1987 | Bosnjakovic | |
| 5,757,006 A | 5/1998 | DeVito et al. | |
| 5,821,541 A | 10/1998 | Tumer | |
| 6,323,492 B1 | 11/2001 | Clinthorne | |
| 6,346,706 B1 | 2/2002 | Rogers et al. | |
| 6,762,413 B2 | 7/2004 | Zeng | |
| 6,791,090 B2 | 9/2004 | Lin et al. | |
| 7,015,477 B2 | 3/2006 | Gunter | |
| 7,045,789 B2 | 5/2006 | Ogawa et al. | |
| 7,262,417 B2 | 8/2007 | Smith | |
| 7,291,841 B2 | 11/2007 | Nelson et al. | |
| 7,304,309 B2 | 12/2007 | Suhami | |
| 7,321,122 B2 | 1/2008 | Bryman | |
| 7,345,283 B2 | 3/2008 | Gunter | |
| 7,504,635 B2 | 3/2009 | Ramsden | |
| 7,550,738 B1 | 6/2009 | DeVito | |
| 7,573,039 B2 | 8/2009 | Smith | |
| 7,667,203 B2 | 2/2010 | Hindi et al. | |
| 7,831,024 B2 | 11/2010 | Metzler et al. | |
| 7,863,567 B1 | 1/2011 | Hynes et al. | |
| 7,928,399 B2 | 4/2011 | Myjak et al. | |
| 8,107,589 B2 | 1/2012 | Sakurai et al. | |
| 8,153,986 B2 | 4/2012 | Mihailescu et al. | |
| 8,217,362 B2 | 7/2012 | DeVito | |
| 8,299,437 B2 | 10/2012 | Nakamura | |
| 8,354,648 B2 | 1/2013 | Laurent et al. | |
| 8,476,595 B2 | 7/2013 | McKinsey et al. | |
| 8,515,011 B2 | 8/2013 | Mundy et al. | |
| 8,519,343 B1 | 8/2013 | Mihailescu et al. | |
| 8,716,669 B2 | 5/2014 | Miyaoka et al. | |
| 8,742,360 B2 | 6/2014 | Yamaguchi et al. | |
| 8,847,166 B2 | 9/2014 | Fukuchi et al. | |
| 2002/0008205 A1 | 1/2002 | Kurfess et al. | |
| 2002/0134942 A1 | 9/2002 | Pehl et al. | |
| 2002/0181654 A1* | 12/2002 | Baertsch | H05G 1/30 378/98 |
| 2003/0128801 A1* | 7/2003 | Eisenberg | A61B 6/466 378/19 |
| 2003/0161526 A1 | 8/2003 | Jupiter et al. | |
| 2003/0205675 A1* | 11/2003 | Nelson | G01T 1/2928 250/370.09 |
| 2004/0084624 A1 | 5/2004 | Meng et al. | |
| 2005/0139775 A1 | 6/2005 | Gono et al. | |
| 2005/0253073 A1 | 11/2005 | Joram et al. | |
| 2007/0205367 A1* | 9/2007 | Deman | G01T 1/2985 250/366 |
| 2007/0253530 A1 | 11/2007 | Mihailescu et al. | |
| 2008/0088059 A1 | 4/2008 | Tang et al. | |
| 2008/0139914 A1 | 6/2008 | Gaved et al. | |
| 2008/0198336 A1* | 8/2008 | Chen | G03B 21/2013 362/373 |
| 2009/0202041 A1 | 8/2009 | Shirahata et al. | |
| 2010/0090117 A1 | 4/2010 | Nelson | |
| 2010/0189222 A1* | 7/2010 | Eaton | G21K 1/025 378/68 |
| 2010/0270462 A1* | 10/2010 | Nelson | G01T 1/2018 250/252.1 |
| 2010/0294945 A1 | 11/2010 | Cussonneau | |
| 2011/0074426 A1* | 3/2011 | Schmand | G01T 1/1603 250/363.04 |
| 2011/0253901 A1 | 10/2011 | Chmeissani et al. | |
| 2011/0303854 A1 | 12/2011 | DeVito | |
| 2012/0043467 A1 | 2/2012 | Gueorguiev et al. | |
| 2012/0128127 A1* | 5/2012 | Chicchetti | G01T 7/00 378/91 |
| 2012/0132814 A1 | 5/2012 | Weinberg | |
| 2012/0217386 A1 | 8/2012 | Ricci et al. | |
| 2012/0290519 A1 | 11/2012 | Fontaine et al. | |
| 2014/0016942 A1* | 1/2014 | Masarik | H04N 5/77 398/130 |
| 2014/0110592 A1 | 4/2014 | Nelson et al. | |
| 2014/0301534 A1* | 10/2014 | Rao | G01T 1/247 250/366 |
| 2014/0361181 A1 | 12/2014 | Liu et al. | |
| 2015/0192685 A1 | 7/2015 | Griesmer et al. | |
| 2015/0331115 A1 | 11/2015 | Nelson et al. | |
| 2016/0070006 A1* | 3/2016 | Konkle | G01T 1/208 250/366 |
| 2016/0077216 A1* | 3/2016 | Hefetz | H05K 7/20418 250/336.1 |
| 2016/0235378 A1* | 8/2016 | Yun | H05G 1/025 |
| 2017/0012308 A1 | 1/2017 | Ikeuchi | |
| 2018/0059270 A1* | 3/2018 | Hefetz | H05K 7/20245 |
| 2018/0095182 A1* | 4/2018 | Su | A61B 6/4488 |
| 2018/0356540 A1* | 12/2018 | Gemba | G01T 1/29 |
| 2019/0216415 A1* | 7/2019 | Wojcik | A61B 6/4233 |

FOREIGN PATENT DOCUMENTS

| | | |
|---|---|---|
| JP | 2011237457 A | 11/2011 |
| WO | 2012077468 A1 | 6/2012 |
| WO | 2018019941 A1 | 2/2018 |

OTHER PUBLICATIONS

International Search Report for Correspondign International Application No. PCT/US2018/045465, dated May 16, 2019.

* cited by examiner

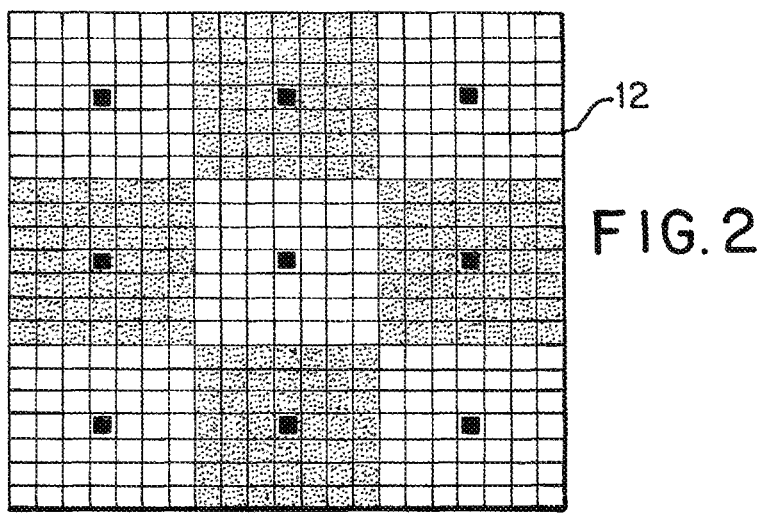
FIG. 2
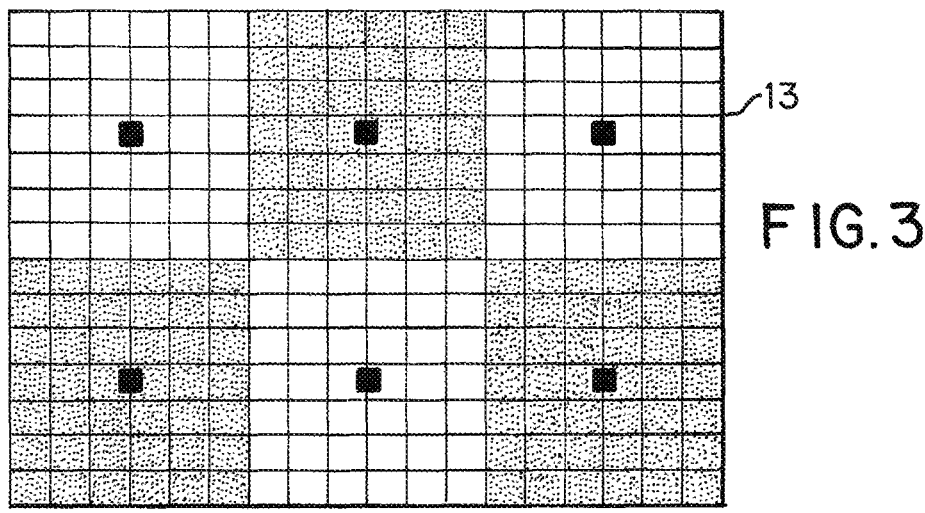
FIG. 3
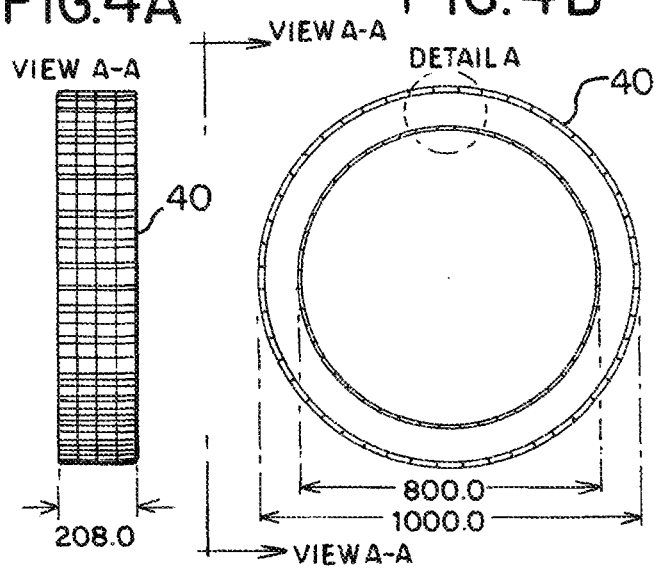
FIG. 4A
FIG. 4B
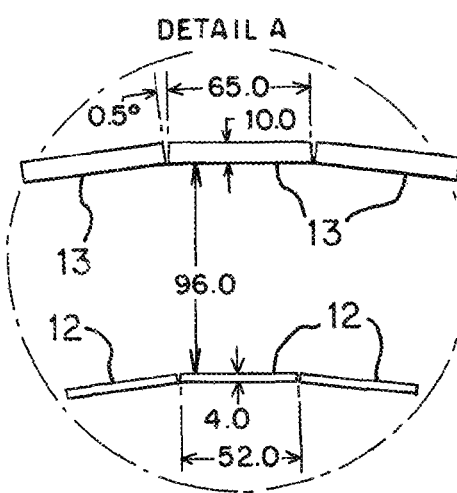
FIG. 4C

COMPTON CAMERA WITH SEGMENTED DETECTION MODULES

BACKGROUND

The present embodiments relate to a Compton medical imaging system. Compton imaging systems are constructed as test platforms, such as assembling a scatter ring and then a catcher ring mounted to a large framework. Electronics are connected to detect Compton-based events from emissions of a phantom. Compton imaging systems have failed to address design and constraint requirements for practical use in any commercial clinical settings. Current proposals lack the ability to be integrated into imaging platforms in the clinic or lack the design and constraint requirements (i.e., flexibility and scalability) to address commercial needs.

SUMMARY

By way of introduction, the preferred embodiments described below include methods, systems, and Compton cameras for medical imaging. The Compton camera is divided into segments with each segment including part of the scatter detector, part of the catcher detector, and part of the electronics. The different segments may be positioned together to form the Compton camera arcing around part of the patient space. By using segments, any number of segments may be used to fit with a multi-modality imaging system.

In a first aspect, a Compton camera is provided for medical imaging. A first module has a wedged cross-section formed by a first housing, a first scatter detector connected with the first housing, and a first catcher detector connected with the first housing and spaced from the first scatter detector. A second module has the same wedged cross-section formed by a second housing, a second scatter detector connected with the second housing, and a second catcher detector connected with the second housing and spaced from the second scatter detector. The first module is connectable and disconnectable with the second module.

In a second aspect, a medical imaging system includes solid state detector modules each with scatter and catcher detectors of a Compton sensor. The solid-state detector modules are shaped to stack together as a ring or partial ring of configurable numbers of the solid-state detector modules.

In a third aspect, a method is provided for forming a Compton camera. Scatter and catcher detector pairs are housed in separate housings shaped to abut where the scatter and catcher detector pairs of different ones of the housings are non-planar. The housings abut in a ring or partial ring around a patient space.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 2 illustrates an example scatter detector;

FIG. 3 illustrates an example catcher detector;

FIG. 4A is a side view of one embodiment of a Compton camera, FIG. 4B is an end view of the Compton camera of FIG. 4A, and FIG. 4C is a detail view of a part of the Compton camera of FIG. 4B;

DETAILED DESCRIPTION OF THE DRAWINGS AND PRESENTLY PREFERRED EMBODIMENTS

Figure 1:
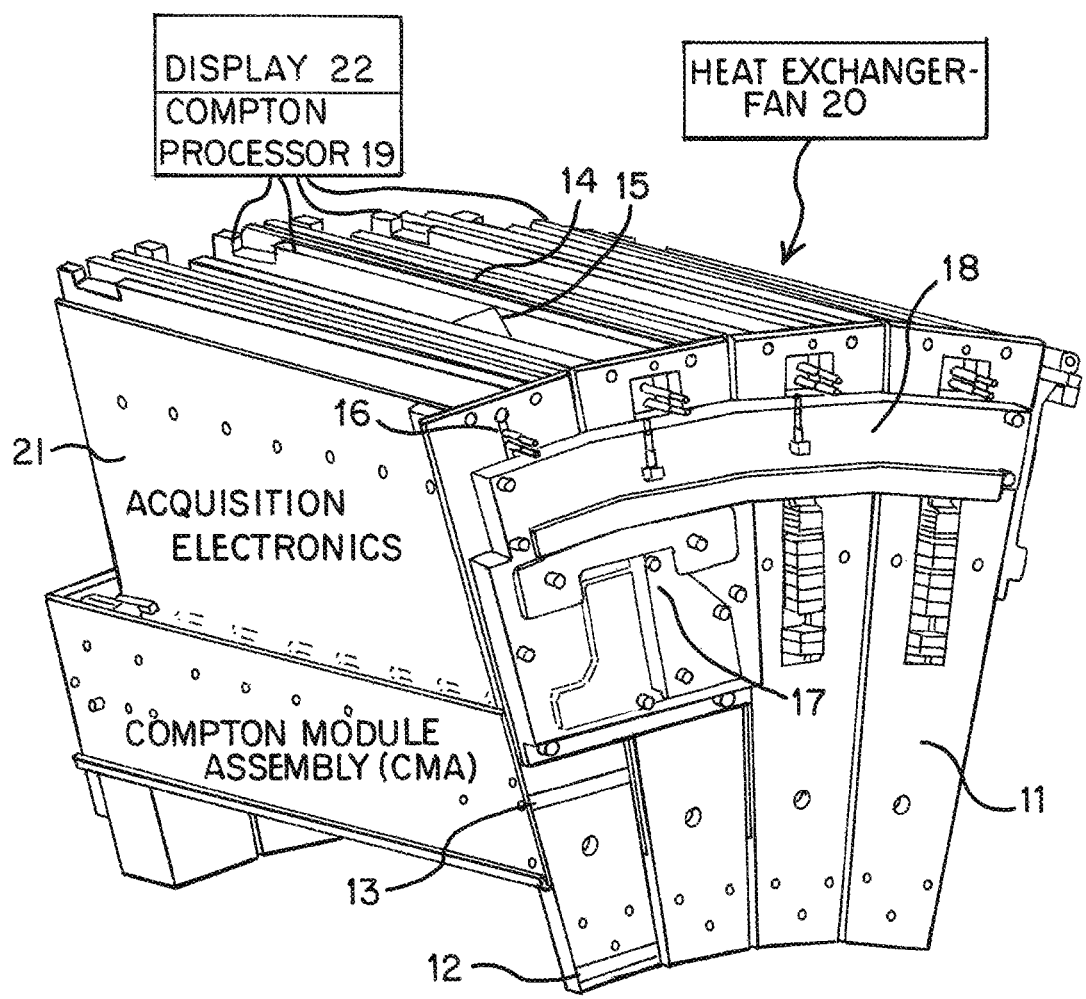
FIG. 1 is perspective view of multiple modules of a Compton camera according to one embodiment.

A medical imaging system includes a multi-modality compatible Compton camera with segmented detection modules. The Compton camera, such as a Compton camera ring, is segmented into modules that house the detection units. Each module is independent, and when assembled into a ring or partial ring, the modules may communicate with each other. The modules are independent yet can be assembled into a multi-module unit that produces Compton scattering-based images. Cylindrically symmetric modules or spherical shell segmented modules may be used.

The scatter-catcher pair, modular arrangement allows efficient manufacturing, is serviceable in the field, and is cost and energy efficient. The modules allow for the design freedom to change the radius for each radial detection unit, angular span of one module, and/or axial span. The scatter-catcher pair modules are multi-modality compatible and/or form a modular ring Compton camera for clinical emission imaging. This design allows flexibility, so the Compton camera may be added to existing computed tomography (CT), magnetic resonance (MR), positron emission tomography (PET) or other medical imaging platforms, either as axially separated systems or as fully integrated systems. Each module may address heat dissipation, data collection, calibration, and/or allow for efficient assembly as well as servicing.

Each scatter-catcher paired module is formed from commercially suitable solid-state detector modules (e.g., Si, CZT, CdTe, HPGe, or similar), allowing for an energy range of 100-3000 keV. Compton imaging may be provided with a wider range of isotope energies (>2 MeV), enabling new tracers/markers through selection of the scatter-catcher detectors. The modularity allows for individual module removal or replacement, allowing for time and cost-efficient service. The modules may be operated independently and isolated or may be linked for cross-talk, allowing for improved image quality and higher efficiency in detecting Compton events using a scatter detector of one module and a catcher detector of another module.

The modularity allows for flexible design geometry optimized to individual requirements, such as using a partial ring for integration with a CT system (e.g., connected between the x-ray source and detector), a few modules (e.g., tiling)

used for integration with a single photon emission computed tomography gamma camera or other space limited imaging system, or a full ring. Functional imaging based on Compton-detected events may be added to other imaging systems (e.g., CT, MR, or PET). Multiple full or partial rings may be placed adjacent to each other for greater axial coverage of the Compton camera. A dedicated or stand-alone Compton-based imaging system may be formed. In one embodiment, the modules include a collimator for lower energies (e.g., <300 keV), providing for multichannel and multiplexed imaging (e.g., high energies using the scatter-catcher detectors for Compton events and low energies using one of the detectors for SPECT or PET imaging). The modules may be stationary or fast rotating (0.1 rpm<<ω<<240 rpm). The dimensional, installation, service, and/or cost constraints are addressed by the scatter-catcher paired modules.

FIG. 1 shows one embodiment of modules 11 for a Compton camera. Four modules 11 are shown, but additional or fewer modules may be used. The Compton camera is formed from one or more modules, depending on the desired design of the Compton camera.

The Compton camera is for medical imaging. A space for a patient relative to the modules is provided so that the modules are positioned to detect photons emitted from the patient. A radiopharmaceutical in the patient includes a radio-isotope. A photon is emitted from the patient due to decay from the radio-isotope. The energy from the radio-isotope may be 100-3000 keV, depending on the material and structure of the detectors. Any of various radio-isotopes may be used for imaging a patient.

Each of the modules 11 includes the same or many of the same components. A scatter detector 12, a catcher detector 13, circuit boards 14, and baffle 15 are provided in a same housing 21. Additional, different, or fewer components may be provided. For example, the scatter detector 12 and catcher detector 13 are provided in the housing 21 without other components. As another example, a fiber optic data line 16 is provided in all or a sub-set of the modules 11.

The modules 11 are shaped for being stacked together. The modules 11 mate with each other, such as having matching indentation and extensions, latches, tongue-and-grooves, or clips. In other embodiments, flat or other surfaces are provided for resting against each other or a divider. Latches, clips, bolts, tongue-and-groove or other attachment mechanisms for attaching a module 11 to any adjacent modules 11 are provided. In other embodiments, the module 11 attaches to a gantry or other framework with or without direct connection to any adjacent modules 11.

The connection or connections to the other modules 11 or gantry may be releasable. The module 11 is connected and may be disconnected. The connection may be releasable, allowing removal of one module 11 or a group of modules 11 without removing all modules 11.

For forming a Compton camera from more than one module 11, the housing 21 and/or outer shape of the modules 11 is wedge shaped. The modules 11 may be stacked around an axis to form a ring or partial ring due to the wedge shape. The part closer to the axis has a width size that is narrower along a dimension perpendicular to the axis than a width size of a part further from the axis. In the modules 11 of FIG. 1, the housings 21 have the widest part furthest from the axis. In other embodiments, the widest part is closer to the axis but spaced away from the narrowest part closest to the axis. In the wedge shape, the scatter detector 12 is nearer to the narrower part of the wedge shape than the catcher detector 13. This wedge shape in cross-section along a plane normal to the axis allows stacking of the modules 11 in abutting positions, adjacently, and/or connected to form at least part of a ring about the axis.

The taper of the wedge provides for a number N of modules 11 to form a complete ring around the axis. Any number N may be used, such as N=10-30 modules. The number N may be configurable, such as using different housings 21 for different numbers N. The number of modules 11 used for a given Compton camera may vary, depending on the design of the Compton camera (e.g., partial ring). The wedge shape may be provided along other dimensions, such as having a wedge shape in a cross-section parallel to the axis.

The modules 11 as stacked are cylindrically symmetric as connected with a gantry of a medical imaging system. A narrowest end of the wedged cross-section is closest to a patient space of the medical imaging system and a widest end of the wedged cross-section may be furthest from the patient space. In alternative embodiments, other shapes than wedge allowing for stacking together to provide a ring or generally curved shape of the stack may be provided.

The housing 21 is metal, plastic, fiberglass, carbon (e.g., carbon fiber), and/or other material. In one embodiment, different parts of the housing 21 are of different materials. For example, tin is used for the housing around the circuit boards 14. Aluminum is used to hold the scatter detector 12 and/or catcher detector 13. In another example, the housing 12 is of the same material, such as aluminum.

The housing 21 may be formed from different structures, such as end plates having the wedge shape, sheets of ground plane housing the circuit boards 14, and separate structure for walls holding the scatter detector 12 and catcher detector 13 where the separate structure is formed of material through which photons of a desired energy from a Compton event may pass (e.g., aluminum or carbon fiber). In alternative embodiments, walls are not provided for the modules 11 between the end plates for a region where the scatter detector 12 and/or catcher detector 13 are positioned, avoiding interference of photons passing from the scatter detector 12 of one module 11 to a catcher detector 13 of another module 11. The housing 21 by and/or for holding the detectors 12, 13 is made of low attenuating material, such as aluminum or carbon fiber.

The housing 21 may seal the module or includes openings. For example, openings for air flow are provided, such as at a top of widest portion of the wedge shape at the circuit boards 14. The housing 21 may include holes, grooves, tongues, latches, clips, stand-offs, bumpers, or other structures for mounting, mating, and/or stacking.

Each of the solid-state detector modules 11 includes both scatter and catcher detectors 12, 13 of a Compton sensor. By stacking each module, the size of the Compton sensor is increased. A given module 11 itself may be a Compton sensor since both the scatter detector 12 and catcher detector 13 are included in the module.

The modules 11 may be separately removed and/or added to the Compton sensor. For a given module 11, the scatter detector 12 and/or catcher detector 13 may be removable from the module 11. For example, a module 11 is removed for service. A faulty one or both detectors 12, 13 are removed from the module 11 for replacement. Once replaced, the refurbished module 11 is placed back in the medical imaging system. Bolts, clips, latches, tongue-and-groove, or other releasable connectors may connect the detectors 12, 13 or part of the housing 21 for the detectors 12, 13 to the rest of the module 11.

The scatter detector 12 is a solid-state detector. Any material may be used, such as Si, CZT, CdTe, HPGe, and/or other material. The scatter detector 12 is created with wafer fabrication at any thickness, such as about 4 mm for CZT. Any size may be used, such as about 5×5 cm. FIG. 2 shows a square shape for the scatter detector 12. Other shapes than square may be used, such as rectangular. For the modules 11 of FIG. 1, the scatter detector 12 may be rectangular extending between two wedge-shaped end-plates.

In the module 11, the scatter detector 12 has any extent. For example, the scatter detector 12 extends from one wedge-shaped end wall to the other wedge-shaped end wall. Lesser or greater extent may be provided, such as extending between mountings within the module 11 or extending axially beyond one or both end-walls. In one embodiment, the scatter detector 12 is at, on, or by one end wall without extended to another end wall.

The scatter detector 12 forms an array of sensors. For example, the 5×5 cm scatter detector 12 of FIG. 2 is a 21×21 pixel array with a pixel pitch of about 2.2 mm. Other numbers of pixels, pixel pitch, and/or size of arrays may be used.

The scatter detector 12 includes semiconductor formatted for processing. For example, the scatter detector 12 includes an application specific integrated circuit (ASIC) for sensing photon interaction with an electron in the scatter detector 12. The ASIC is collocated with the pixels of the scatter detector 12. The ASIC is of any thickness. A plurality of ASICs may be provided, such as 9 ASICS in a 3×3 grid of the scatter detector 12.

The scatter detector 12 may operate at any count rate, such as >100 kcps/mm. Electricity is generated by a pixel due to the interaction. This electricity is sensed by the application specific integrated circuit. The location, time, and/or energy is sensed. The sensed signal may be conditioned, such as amplified, and sent to one or more of the circuit boards 14. A flexible circuit, wires, or other communications path carries the signals from the ASIC to the circuit board 14.

Compton sensing operates without collimation. Instead, a fixed relationship between energy, position, and angle of a photon interaction at the scatter detector 12 relative to a photon interaction at the catcher detector 13 is used to determine the angle of the photon entering the scatter detector 12. A Compton process is applied using the scatter detector 12 and the catcher detector 13.

The catcher detector 13 is a solid-state detector. Any material may be used, such as Si, CZT, CdTe, HPGe, and/or other material. The catcher detector 13 is created with wafer fabrication at any thickness, such as about 10 mm for CZT. Any size may be used, such as about 5×5 cm. The size may be larger along at least one dimension than the scatter detector 12 due to the wedge shape and spaced apart positions of the scatter detector 12 and the catcher detector 13. FIG. 3 shows a rectangular shape for the catcher detector 13 but other shapes may be used. For the modules 11 of FIG. 1, the catcher detector 13 may be rectangular extending between two end-plates where the length is the same as and the width is greater than the scatter detector 12.

The catcher detector 12 forms an array of sensors. For example, the 5×6 cm catcher detector 13 of FIG. 3 is a 14×18 pixel array with a pixel pitch of about 3.4 mm. The pixel size is larger than the pixel size of the scatter detector 12. The number of pixels is less than the number of pixels of the scatter detector 12. Other numbers of pixels, pixel pitch, and/or size of arrays may be used. Other relative pixels sizes and/or numbers of pixels may be used.

In the module 11, the catcher detector 13 has any extent. For example, the catcher detector 13 extends from one wedge-shaped end wall to the other wedge-shaped end wall. Lesser or greater extent may be provided, such as extending between mountings within the module 11 or extending axially beyond one or both end-walls. In one embodiment, the catcher detector 13 is at, on, or by one end wall without extending to another end wall.

The catcher detector 13 includes semiconductor formatted for processing. For example, the catcher detector 13 includes an ASIC for sensing photon interaction with an electron in the catcher detector 13. The ASIC is collocated with the pixels of the catcher detector 13. The ASIC is of any thickness. A plurality of ASICS may be provided, such as 6 ASICS in a 2×3 grid of the catcher detector 13.

The catcher detector 13 may operate at any count rate, such as >100 kcps/mm. Electricity is generated by a pixel due to the interaction. This electricity is sensed by the ASIC. The location, time, and/or energy is sensed. The sensed signal may be conditioned, such as amplified, and sent to one or more of the circuit boards 14. A flexible circuit, wires, or other communications path carries the signals from the ASIC to the circuit board 14.

The catcher detector 13 is spaced from the scatter detector 12 by any distance along a radial line from the axis or normal to the parallel scatter and catcher detectors 12, 13. In one embodiment, the separation is about 20 cm, but greater or lesser separation may be provided. The space between the catcher detector 13 and the scatter detector 12 is filled with air, other gas, and/or other material with low attenuation for photons at the desired energies.

The circuit boards 14 are printed circuit boards, but flexible circuits or other materials may be used. Any number of circuit boards 14 for each module may be used. For example, one circuit board 14 is provided for the scatter detector 12 and another circuit board 14 is provided for the catcher detector 13.

The circuit boards 14 are within the housing 21 but may extend beyond the housing 21. The housing 21 may be grounded, acting as a ground plane for the circuit boards 14. The circuit boards 14 are mounted in parallel with each other or are non-parallel, such as spreading apart in accordance with the wedge shape. The circuit boards are positioned generally orthogonal to the catcher detector 13. Generally is used to account for any spread due to the wedge shape. Brackets, bolts, screws, and/or stand-offs from each other and/or the housing 21 are used to hold the circuit boards 14 in place.

The circuit boards 14 connect to the ASICS of the scatter and catcher detectors 12, 13 through flexible circuits or wires. The ASICs output detected signals. The circuit boards 14 are acquisition electronics, which process the detected signals to provide parameters to the Compton processor 19 (e.g., image processor). Any parameterization of the detected signals may be used. In one embodiment, the energy, arrival time, and position in three-dimensions is output. Other acquisition processing may be provided.

The circuit boards 14 output to each other, such as through a galvanic connection within a module 11, to the data bridge 17, and/or to a fiber optic data link 16. The fiber data link 16 is a fiber optic interface for converting electrical signals to optical signals. A fiber optic cable or cables provide the acquisition parameters for events detected by the scatter and catcher detectors 12, 13 to the Compton processor 19.

The data bridge 17 is a circuit board, wires, flexible circuit, and/or other material for galvanic connection to allow communications between modules 11. A housing or protective plate may cover the data bridge 17. The data bridge 17 releasably connects to one or more modules 11. For example, plugs or mated connectors of the data bridge 17 mate with corresponding plugs or mated connectors on the housing 21 and/or circuit boards 14. A latch, clip, tongue-and-groove, screw, and/or bolt connection may be used to releasably hold the data bridge 17 in place with the modules 11.

The data bridge 17 allows communications between the modules. For example, the fiber data link 16 is provided in one modules 11 and not another module 11. The cost of a fiber data link 16 in every module 11 is avoided. Instead, the parameters output by the other module 11 are provided via the data bridge 17 to the module 11 with the fiber data link 16. The circuit board or boards 14 of the module 11 with the fiber data link 16 route the parameter output to the fiber data link 16, using the fiber data link 16 to report detected events from more than one module 11. In alternative embodiments, each module 11 includes a fiber data link 16, so the data bridge 17 is not provided or communicates other information.

The data bridge 17 may connect other signals between the modules 11. For example, the data bridge 17 includes a conductor for power. Alternatively, a different bridge provides power to the modules 11 or the modules 11 are individually powered. As another example, clock and/or synchronization signals are communicated between modules 11 using the data bridge 17.

In the embodiment of FIG. 1, a separate clock and/or synchronization bridge 18 is provided. The clock and/or synchronization bridge 18 is a circuit board, wires, flexible circuit, and/or other material for galvanic connection to allow communication of clock and/or synchronization signals between modules 11. A housing or protective plate may cover the clock and/or synchronization bridge 18. The clock and/or synchronization bridge 18 releasably connects to one or more modules 11. For example, plugs or mated connectors of the clock and/or synchronization bridge 18 mate with corresponding plugs or mated connectors on the housing 21 and/or circuit boards 14. A latch, clip, tongue-and-groove, screw, and/or bolt connection may be used to releasably hold the clock and/or synchronization bridge 18 in place with the modules 11.

The clock and/or synchronization bridge 18 may connect with the same or different grouping of modules 11 as the data bridge 17. In the embodiment shown in FIG. 1, the data bridge 17 connects between pairs of modules 11 and the clock and/or synchronization bridge 18 connects over groups of four modules 11.

The clock and/or synchronization bridge 18 provides a common clock signal and/or synchronization signals for synchronizing clocks of the modules 11. One of the parameters formed by the circuit boards 14 of each module 11 is the time of detection of the event. Compton detection relies on pairs of events—a scatter event and a catcher event. Timing is used to pair events from the different detectors 12, 13. The common clocking and/or synchronization allows for accurate pairing where the pair of events are detected in different modules 11. In alternative embodiments, only scatter and catcher events detected in a same module 11 are used, so the clock and/or synchronization bridge 18 may not be provided.

Other links or bridges between different modules 11 may be provided. Since the bridges 17, 18 are removable, individual modules 11 may be removed for service while leaving remaining modules 11 in the gantry.

Each module 11 is air cooled. Holes may be provided for forcing air through the module 11 (i.e., entry and exit holes). One or more baffles 15 may be provided to guide the air within the module 11. Water, conductive transfer, and/or other cooling may be alternatively or additionally provided.

In one embodiment, the top portion of the wedge-shape module 11 or housing 21 is open (i.e., no cover on the side furthest from the patient area). One or more baffles 15 are provided along the centers of one or more circuit boards 14 and/or the housing 21. A fan and heat exchanger 20 force cooled or ambient temperature air into each module 11, such as along one half of the module 11 at a location spaced away from the catcher detector 13 (e.g., top of the module 11). The baffles 15 and/or circuit boards 14 guide at least some of the air to the airspace between the scatter detector 12 and the catcher detector 13. The air then passes by the baffles 15 and/or circuit boards 14 on another part (e.g., another half) of the module 11 for exiting to the heat exchanger 20. Other routing of the air may be provided.

The heat exchanger and fan 20 is provided for each individual module 11, so may be entirely or partly within the module 11. In other embodiments, ducting, baffles, or other structure route air to multiple modules 11. For example, groups of four modules 11 share a common heat exchanger and fan 20, which is mounted to the gantry or other framework for cooling the group of modules 11.

For forming a Compton sensor, one or more modules 11 are used. For example, two or more modules 11 are positioned relative to a patient bed or imaging space to detect photon emissions from the patient. An arrangement of a greater number of modules 11 may allow for detection of a greater number of emissions. By using the wedge shape, modules 11 may be positioned against, adjacent, and/or connected with each other to form an arc about the patient space. The arc may have any extent. The modules 11 directly contact each other or contact through spacers or the gantry with small separation (e.g., 10 cm or less) between the modules 11.

In one example, four modules 11 are positioned together, sharing a clock and/or synchronization bridge 18, one or more data bridges 17, and a heat exchanger and fan 20. One, two, or four fiber data links 16 are provided for the group of modules 11. Multiple such groups of modules 11 may be positioned apart or adjacent to each other for a same patient space.

Due to the modular approach, any number of modules 11 may be used. Manufacturing is more efficient and costly by building multiple of the same component despite use of any given module 11 in a different arrangement than used for others of the modules 11.

The fiber data links 16 of the modules 11 or groups of modules 11 connect to the Compton processor 19. The Compton processor 19 receives the values for the parameters for the different events. Using the energy and timing parameters, scatter and catcher events are paired. For each pair, the spatial locations and energies of the pair of events are used to find the angle of incidence of the photon on the scatter detector 12. The event pairs are limited to events in the same module 11 in one embodiment. In another embodiment, catcher events from the same or different modules 11 may be paired with scatter events from a given module 11. More than one Compton processor 19 may be used, such as for pairing events from different parts of a partial ring 40.

Once paired events are linked, the Compton processor 19 or another processor may perform computed tomography to reconstruct a distribution in two or three dimensions of the detected emissions. The angle or line of incidence for each event is used in the reconstruction. The reconstructed distribution of detected Compton events is used to render a Compton image.

The display 22 is a CRT, LCD, projector, printer, or other display. The display 22 is configured to display the Compton image. The image or images are stored in a display plane buffer and read out to the display 22. The images may be displayed separately or are combined, such as displaying the Compton image overlaid with or adjacent to the SPECT image.

Figure 5:
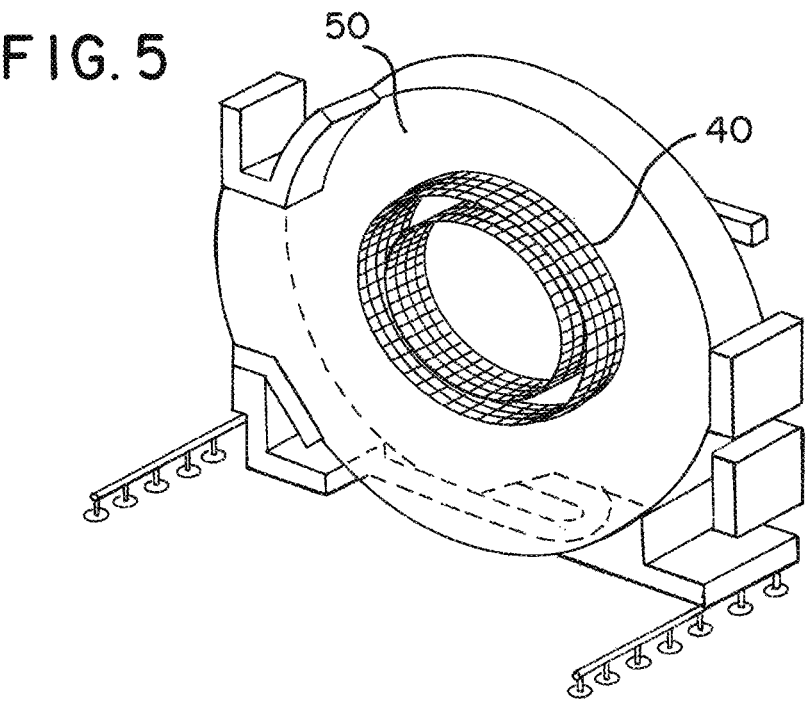
FIG. 5 is a perspective view of one embodiment of a Compton camera in a medical imaging system.
Figure 6:
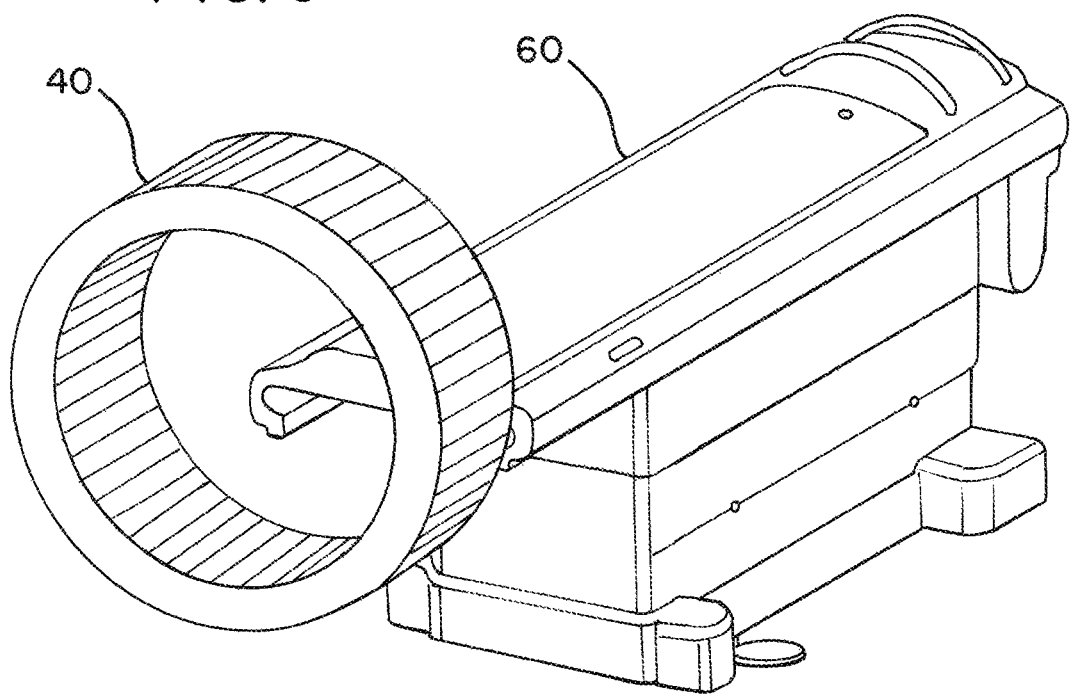
FIG. 6 is a perspective view of one embodiment of a full-ring Compton camera in a medical imaging system.

FIGS. 4A-6 shows one example arrangement of modules 11. The modules 11 form a ring 40 surrounding a patient space. FIG. 4A shows four such rings 40 stacked axially. FIG. 4B shows the scatter detectors 12 and corresponding catcher detectors 13 of the modules 11 in the ring 40. FIG. 4C shows a detail of a part of the ring 40. Three modules 11 provide corresponding pairs of scatter and catcher detectors 12, 13. Other dimensions than shown may be used. Any number of modules 11 may be used to form the ring 40. The ring 40 completely surrounds the patient space. Within a housing of a medical imaging system, the ring 40 connects with a gantry 50 or another framework as shown in FIG. 5. The ring 40 may be positioned to allow a patient bed 60 to move a patient into and/or through the ring 40. FIG. 6 shows an example of this configuration.

Figure 7:
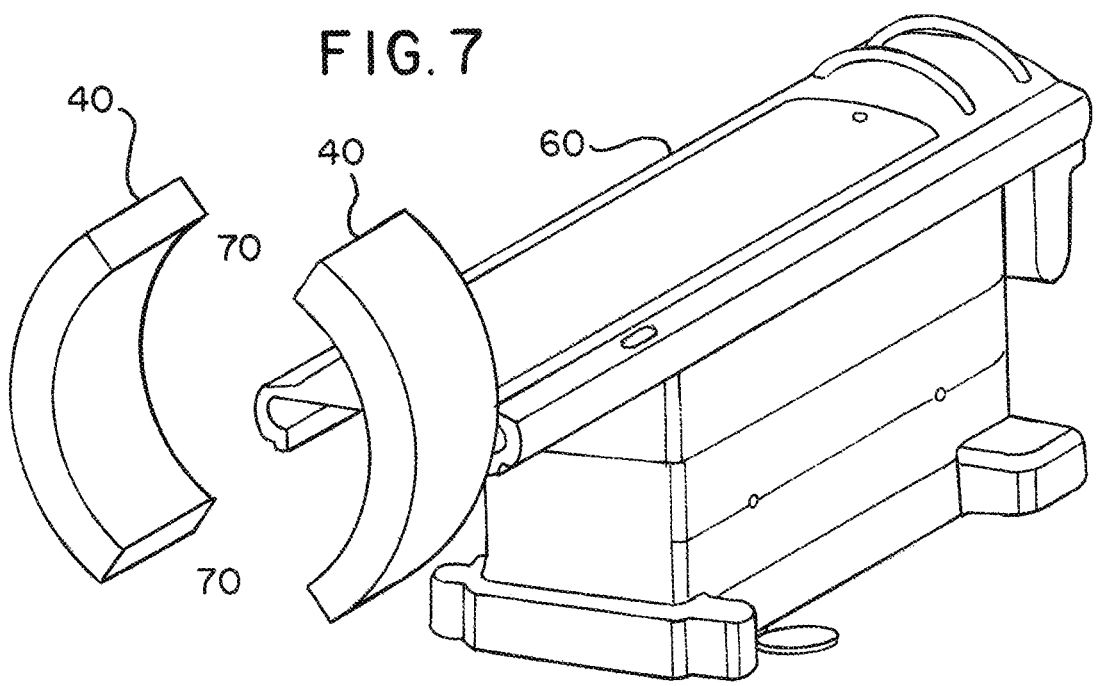
FIG. 7 is a perspective view of one embodiment of a partial-ring Compton camera in a medical imaging system.

The ring may be used for Compton-based imaging of emissions from a patient. FIG. 7 shows an example of using the same type of modules 11 but in a different configuration. A partial ring 40 is formed. One or more gaps 70 are provided in the ring 40. This may allow for other components to be used in the gaps and/or to make a less costly system by using fewer modules 11.

Figure 8:
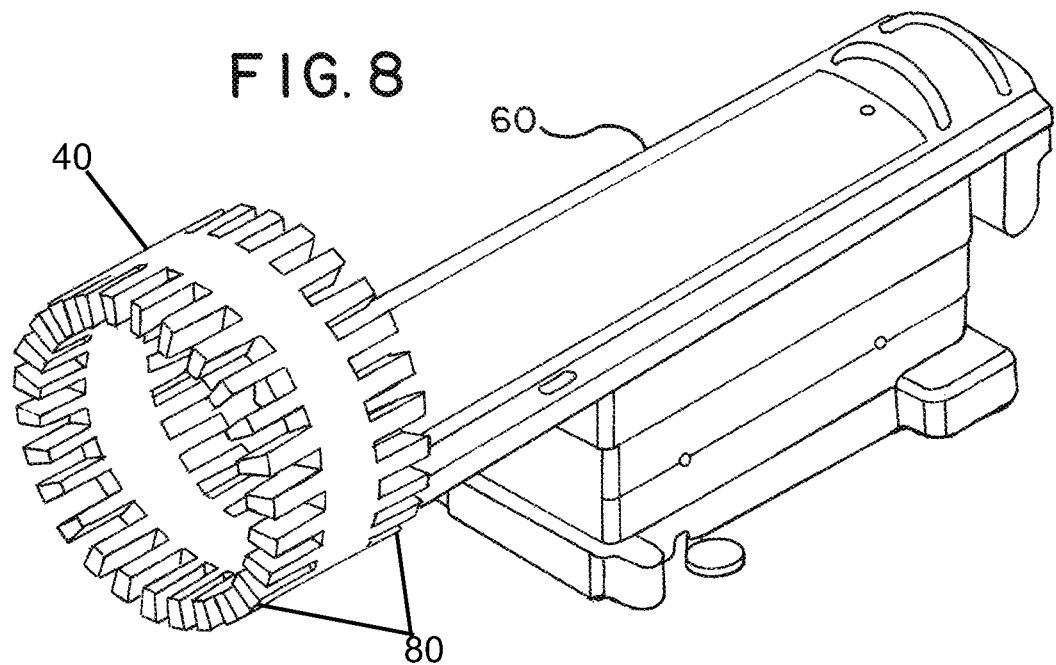
FIG. 8 is a perspective view of one embodiment of a full-ring Compton camera with partial-rings in axial extension in a medical imaging system.

FIG. 8 shows another configuration of modules 11. The ring 40 is a full ring. Additional partial rings 80 are stacked axially relative to the bed 60 or patient space, extending the axial extent of detected emissions. The partial rings 80 are in an every other or every group of N modules 11 (e.g., N=4) distribution rather than the two gaps 70 partial ring 40 of FIG. 7. The additional rings may be full rings. The full ring 40 may be a partial ring 80. The different rings 40 and/or partial rings 80 are stacked axially with no or little (e.g., less than ½ a module's 11 axial extent) apart. Wider spacing may be provided, such as having a gap of more than one module's 11 axial extent.

Figure 9:
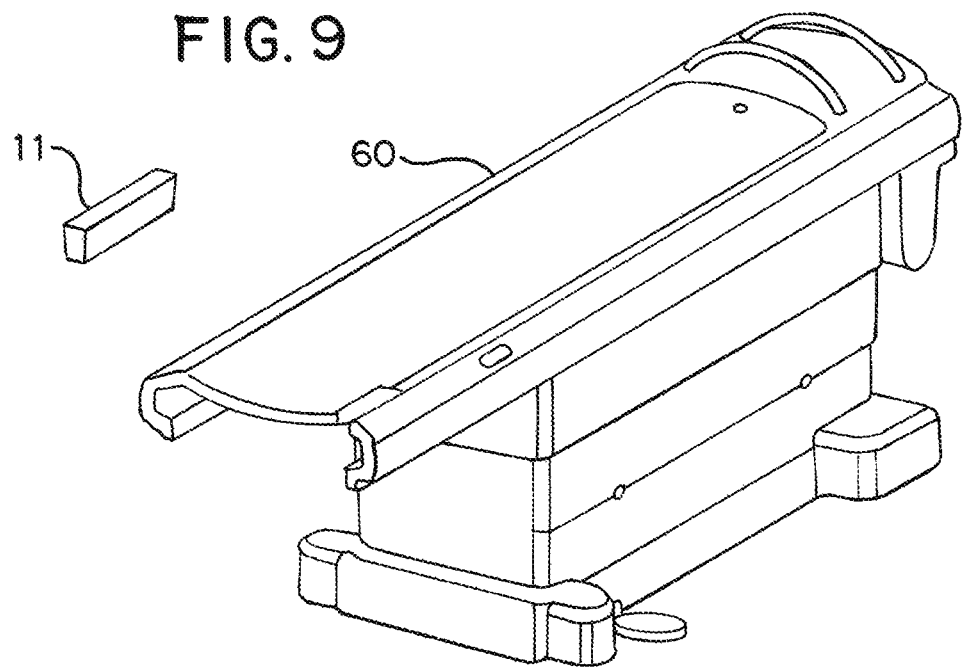
FIG. 9 is a perspective view of one embodiment of a single module-based Compton camera in a medical imaging system.

FIG. 9 shows yet another configuration of modules 11. One module 11 or a single group of modules 11 is positioned by the patient space or bed 60. Multiple spaced apart single modules 11 or groups (e.g., group of four) may be provided at different locations relative to the bed 60 and/or patient space.

In any of the configurations, the modules 11 are held in position by attachment to a gantry, gantries, and/or other framework. The hold is releasable, such as using bolts or screws. The desired number of modules 11 are used to assemble the desired configuration for a given medical imaging system. The gathered modules 11 are mounted in the medical imaging system, defining or relative to the patient space. The result is a Compton sensor for imaging the patient.

The bed 60 may move the patient to scan different parts of the patient at different times. Alternatively or additionally, the gantry 50 moves the modules 11 forming the Compton sensor. The gantry 50 translates axially along the patient space and/or rotates the Compton sensor around the patient space (i.e., rotating about the long axis of the bed 60 and/or patient). Other rotations and/or translations may be provided, such as rotating the modules 11 about an axis non-parallel to the long axis of the bed 60 or patient. Combinations of different translations and/or rotations may be provided.

The medical imaging system with the Compton sensor is used as a stand alone imaging system. Compton sensing is used to measure distribution of radiopharmaceutical in the patient. For example, the full ring 40, partial ring 40, and/or axially stacked rings 40, 80 are used as a Compton-based imaging system.

In other embodiments, the medical imaging system is a multi-modality imaging system. The Compton sensor formed by the modules 11 is one modality, and another modality is also provided. For example, the other modality is a single photon emission computed tomography (SPECT), a PET, a CT, or a MR imaging system. The full ring 40, partial ring 40, axially stacked rings 40,80, and/or singular module 11 or group of modules 11 are combined with the sensors for the other type of medical imaging. The Compton sensor may share a bed 60 with the other modality, such as being positioned along a long axis of the bed 60 where the bed positions the patient in the Compton sensor in one direction and in the other modality in the other direction.

The Compton sensor may share an outer housing with the other modality. For example, the full ring 40, partial ring 40, axially stacked rings 40,80, and/or singular module 11 or group of modules 11 are arranged within a same imaging system housing for the sensor or sensors of the other modality. The bed 60 positions the patient within the imaging system housing relative to the desired sensor. The Compton sensor may be positioned adjacent to the other sensors axially and/or in a gap at a same axial location. In one embodiment, the partial ring 40 is used in a computed tomography system. The gantry holding the x-ray source and the x-ray detector also holds the modules 11 of the partial ring 40. The x-ray source is in one gap 70, and the detector is in another gap 70. In another embodiment, the single module 11 or a sparse distribution of modules 11 connects with a gantry of a SPECT system. The module 11 is placed adjacent to the gamma camera, so the gantry of the gamma camera moves the module 11. Alternatively, a collimator may be positioned between the modules 11 and the patient or between the scatter and catcher detectors 12, 13, allowing the scatter and/or catcher detectors 12, 13 of the modules 11 to be used for photoelectric event detection for SPECT imaging instead of or in addition to detection of Compton events.

The module-based segmentation of the Compton sensor allows the same design of modules 11 to be used in any different configurations. Thus, a different number of modules 11, module position, and/or configuration of modules 11 may be used for different medical imaging systems. For example, one arrangement is provided for use with one type of CT system and a different arrangement (e.g., number and/or position of modules 11) is used for a different type of CT system.

The module-based segmentation of the Compton sensor allows for more efficient and costly servicing. Rather than replacing an entire Compton sensor, any module 11 may be disconnected and fixed or replaced. The modules 11 are individually connectable and disconnectable from each other and/or the gantry 50. Any bridges are removed, and then the module 11 is removed from the medical imaging system while the other modules 11 remain. It is cheaper to replace an individual module 11. The amount of time to service may be reduced. Individual components of a defective module 11 may be easily replaced, such as replacing a scatter or catcher detector 12, 13 while leaving the other. The modules 11 may be configured for operation with different radioisotopes (i.e., different energies) by using corresponding detectors 12, 13.

Figure 10:
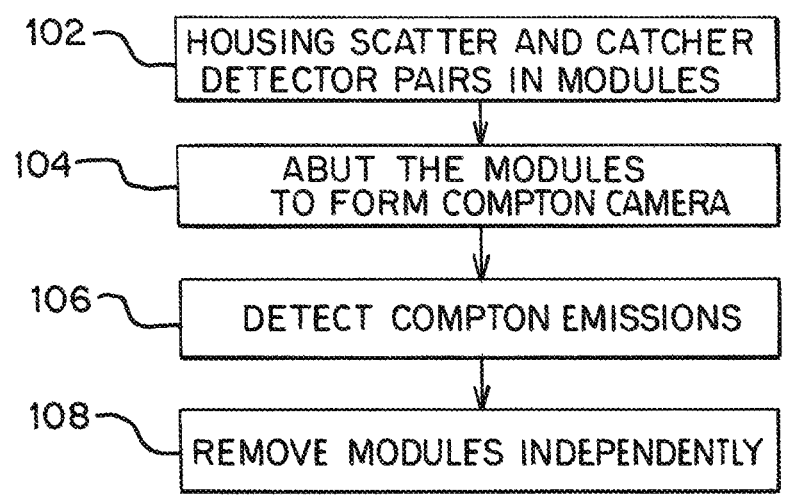
FIG. 10 is a flow chart diagram of an example embodiment of a method for forming a Compton camera.

FIG. 10 shows one embodiment of a flow chart of a method for forming, using, and repairing a Compton camera. The Compton camera is formed in a segmented approach. Rather than hand assembling the entire camera in place, scatter detector and catcher detector pairs are positioned relative to each other to form a desired configuration of the Compton camera. This segmented approach may allow different configurations using the same parts, ease of assembly, ease of repair, and/or integration with other imaging modalities.

The method is implemented by the system of FIG. 1 to assemble a Compton sensor as shown in any of FIGS. 4-9. Other systems, modules, and/or configured Compton sensors may be used.

The acts are performed in the order shown (i.e., top to bottom or numerically) or other orders. For example, act 108 may be performed as part of act 104.

Additional, different, or fewer acts may be provided. For example, acts 102 and 104 are provided for assembling the Compton camera without performing acts 106 and 108. As another example, act 106 is performed without other acts.

In act 102, scatter and catcher detector pairs are housed in separate housings. Modules are assembled where each module includes both a scatter detector and a catcher detector. A machine and/or person manufactures the housings.

The modules are shaped to abut where the scatter and catcher detector pairs of different ones of the housings are non-planar. For example, a wedge shape and/or positioning is provided so that the detector pairs from an arc, such as shown in FIG. 4C. The shape allows and/or forces the arc shape when the modules are positioned against one another.

In act 104, the housings are abutted. A person or machine assembles the Compton sensor from the housings. By stacking the housings adjacent to each other with direct contact or contact through spacers, gantry, or framework, the abutted housings form the arc. A full ring or partial ring is formed around and at least in part defines a patient space. Based on the design of the Compton camera, any number of housings with the corresponding scatter and catcher detector pairs are positioned together to form a Compton camera.

The housings may be abutted as part of a multi-modality system or to create a single Compton imaging system. For a multi-modality system, the housings are positioned in a same outer housing and/or relative to a same bed as the sensors for the other modality, such as SPECT, PET, CT, or MR imaging system. The same or different gantry or support framework may be used for the housings of the Compton camera and the sensors for the other modality.

The configuration or design of the Compton camera defines the number and/or position of the housings. Once abutted, the housings may be connected for communications, such as through one or more bridges. The housings may be connected with other components, such as an air cooling system and/or a Compton processor.

In act 106, the assembled Compton camera detects emissions. A given emitted photon interacts with the scatter detector. The result is scattering of another photon at a particular angle from the line of incidence of the emitted photon. This secondary photon has a lesser energy. The secondary photon is detected by the catcher detector. Based on the energy and timing of both the detected scatter event and catcher event, the events are paired. The positions and energies for the paired events provides a line between the detectors and an angle of scattering. As a result, the line of incidence of the emitted photon is determined.

To increase the likelihood of detecting the secondary photon, the catcher events from one housing may be paired with the scatter events of another housing. Due to the angles, scatter from one scatter detector may be incident on the paired catcher detector in the same housing or a catcher detector in another housing. By the housings being open in the detector region and/or using low photon attenuating materials, a greater number of Compton events may be detected.

The detected events are counted or collected. The lines of response or lines along which the different Compton events occur are used in reconstruction. The distribution in three dimensions of the emissions from the patient may be reconstructed based on the Compton sensing. The reconstruction does not need a collimator as the Compton sensing accounts for or provides the angle in incidence of the emitted photon.

The detected events are reconstructed into object space. An image may be rendered to a display device from the reconstructed events. The image represents a distribution of emissions within the patient.

In act 108, a person or machine (e.g., robot) removes one of the housings. When one of the detectors or associated electronics of a housing fails or is to be replaced for detecting at different energies, the housing may be removed. The other housings are left in the medical imaging system. This allows for easier repair and/or replacement of the housing and/or detectors without the cost of a greater disassembly and/or replacement of the entire Compton camera.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A Compton camera for medical imaging, the Compton camera comprising:
    a first module having a wedged cross-section formed by a first housing, a first scatter detector connected with the first housing, and a first catcher detector connected with the first housing and spaced from the first scatter detector; and
    a second module having the same wedged cross-section formed by a second housing, a second scatter detector connected with the second housing, and a second catcher detector connected with the second housing and spaced from the second scatter detector;
    wherein the first module is connectable and disconnectable by releasable attachment of the first module to the second module, the first module abutted to the second module when connected.

2. The Compton camera of claim 1 wherein the first and second modules are cylindrically symmetric as connected with a gantry of a medical imaging system, a narrowest end of the wedged cross-section being closest to a patient space of the medical imaging system, a widest end of the wedged cross-section being furthest from the patient space, the first module removable from the medical imaging system while the second module remains in the medical imaging system.

3. The Compton camera of claim 1 wherein the first module further comprises circuit boards within the first housing, the circuit boards being orthogonal to the first catcher detector, further comprises application specific integrated circuits with the first scatter detector and the first catcher detector, and further comprises flexible circuits connecting the application specific integrated circuits to the circuit boards.

4. The Compton camera of claim 3 wherein the first module further comprises a baffle with airflow cooling for air entering by the circuit boards and spaced away from the first scatter detector and first catcher detector, passing between the first scatter detector and the first catcher detector, and exiting by the circuit boards.

5. The Compton camera of claim 4 further comprising a heat exchanger and fan shared by the first and second module for the airflow cooling.

6. The Compton camera of claim 1 wherein a power and data bridge connects between the first and second modules, and wherein the first module includes a fiber data link for output of data from the first and second modules and the second module is free of any fiber data link.

7. The Compton camera of claim 1 further comprising third and fourth modules and a clock bridge linking the first, second, third and fourth modules, the third module comprising a wedged cross-section formed by a third housing, a third scatter detector connected with the third housing, and a third catcher detector connected with the third housing and spaced from the third scatter detector, and the fourth module comprising a wedged cross-section formed by a fourth housing, a fourth scatter detector connected with the fourth housing, and a fourth catcher detector connected with the fourth housing and spaced from the fourth scatter detector.

8. The Compton camera of claim 1 wherein the first and second modules form part of a ring or partial ring around a patient space of a medical imaging system.

9. The Compton camera of claim 8 wherein the ring or partial ring share an outer housing of the medical imaging system with an imaging system, which is another modality of medical imaging than the medical imaging system.

10. The Compton camera of claim 8 wherein the ring or partial ring connect to a gantry for moving the ring or partial ring relative to the patient space.

11. The Compton camera of claim 8 further comprising an additional ring or partial ring of modules axially adjacent to the ring or partial ring with the first and second modules.

12. The Compton camera of claim 1 wherein the first and second modules are connected with a single photon emission computed tomography, a positron emission tomography, a computed tomography, or a magnetic resonance imaging system.

13. The Compton camera of claim 1 further comprising a Compton processor communicatively connected to the first and second modules, the Compton processor configured to link a scatter event of the first module with a catcher event of the second module.

14. A medical imaging system comprising:
solid-state detector modules each with scatter and catcher detectors of a Compton sensor, the scatter and catcher detectors of each solid-state detector module formed from solid-state material as plates extending from a first end-plate to a second end-plate of the solid-state detector module, the plates positioned perpendicular to a center axis along a longest dimension of the solid-state detector module;
the solid-state detector modules being shaped to stack together as a ring or partial ring of configurable numbers of the solid-state detector modules.

15. The medical imaging system of claim 14 wherein each of the solid-state detector modules has a wedge shape with the scatter detector nearer to a narrower part of the wedge shape than the catcher detector, an air region separating the scatter detector from the catcher detector.

16. The medical imaging system of claim 14 further comprising a single photon emission computed tomography, a positron emission tomography, a computed tomography, or a magnetic resonance imaging system imager sharing a housing or bed with the solid-state detector modules.

17. The medical imaging system of claim 14 wherein the solid-state detector modules are individually removable from the ring or partial ring when stacked together.

18. A method for forming a Compton camera, the method comprising:
housing scatter and catcher detector pairs in separate housings shaped to directly abut where the scatter and catcher detector pairs of different ones of the housings are non-planar;
abutting the housings in a ring or partial ring around a patient space;
connecting the separate housings together; and
removing one housing from the ring or partial ring while leaving others of the separate housings in the ring or partial ring, the removing including disconnecting the one housing from at least one of the others of the separate housings.

19. The method of claim 18 wherein abutting comprises forming the ring or partial ring as part of a multi-modality system including the Compton camera and a single photon emission computed tomography, a positron emission tomography, a computed tomography, or a magnetic resonance imaging system.

20. The method of claim 18 further comprising detecting an emission with a scatter detector of one housing and a catcher detector of another housing.

* * * * *